United States Patent [19]

McClune et al.

[11] Patent Number: 5,017,474

[45] Date of Patent: May 21, 1991

[54] WASH SOLUTION, TEST KIT AND METHOD FOR THE DETERMINATION OF AN IMMUNOLOGICAL LIGAND

[75] Inventors: Gregory J. McClune, Portage, Mich.; Margaret J. Smith-Lewis, Pittsford, N.Y.

[73] Assignee: Eastman Kodak Company, Rochester, N.Y.

[21] Appl. No.: 155,670

[22] Filed: Feb. 12, 1988

[51] Int. Cl.$^5$ .................... G01N 33/53; G01N 33/48; G01N 33/543; G01N 33/536

[52] U.S. Cl. .................................. 435/7.5; 435/810; 435/975; 435/7.92; 436/501; 436/510; 436/518; 436/531; 436/536; 436/538; 436/543; 436/547; 436/65; 436/808; 436/809; 436/818; 436/824; 436/826; 252/550

[58] Field of Search .................... 435/810, 7; 436/803, 436/501, 510, 518, 531, 65, 808, 809, 818, 826, 536, 538, 543, 547, 177, 824; 252/550

[56] References Cited

U.S. PATENT DOCUMENTS

| | | | |
|---|---|---|---|
| 4,492,762 | 1/1985 | Wang et al. | 436/537 |
| 4,496,654 | 1/1985 | Katz et al. | 436/818 |
| 4,663,291 | 5/1987 | Rose | 435/259 |
| 4,668,640 | 5/1987 | Wang et al. | 436/536 |
| 4,683,136 | 7/1987 | Milich et al. | 435/7 |
| 4,693,985 | 9/1987 | Degen et al. | 436/531 |
| 4,921,915 | 5/1990 | Dengler et al. | 435/7 |

FOREIGN PATENT DOCUMENTS

| | | | |
|---|---|---|---|
| 0109856 | 5/1984 | European Pat. Off. | 436/818 |
| 201079 | 11/1986 | European Pat. Off. | |
| 0302715 | 2/1989 | European Pat. Off. | |
| 87/03690 | 6/1987 | PCT Int'l Appl. | |
| 1572220 | 7/1980 | United Kingdom. | |

OTHER PUBLICATIONS

Qualitiere et al., J. Immun., 119, pp. 1645–1651 (1977).

Primary Examiner—Esther L. Kepplinger
Assistant Examiner—Florina B. Hoffer
Attorney, Agent, or Firm—J. Lanny Tucker

[57] ABSTRACT

An aqueous wash solution is buffered to a pH of from about 5 to about 9 and contains at least about 0.01 weight percent of a compound comprising a dodecyl sulfate anion and an alkali metal or ammonium cation, such as sodium dodecyl sulfate. This wash solution is particularly useful in a method for the determination of an immunological ligand. Particularly, it is useful for washing the immunological complex formed between the ligand and a receptor molecule therefor. Unreacted materials can be readily separated from the complex by the washing, particularly if the separation is carried out using a filtration membrane in a test device. a test kit for ligand determination comprises the wash solution as well as one or more receptors for the ligand, at least one of which is labeled for detection. This kit is particularly useful for measuring human chorionic gonadotropin (hCG) as an early indicator of pregnancy.

11 Claims, No Drawings

WASH SOLUTION, TEST KIT AND METHOD FOR THE DETERMINATION OF AN IMMUNOLOGICAL LIGAND

FIELD OF THE INVENTION

The present invention relates to a wash solution, test kit and method useful for the determination of an immunological ligand, such as human chorionic gonadotropin (hCG) in fluid specimens, such as biological fluids.

BACKGROUND OF THE INVENTION

There is a continuous need in medical practice, research and diagnostic procedures for rapid, accurate and qualitative or quantitative determinations of biological substances which are present in biological fluids at low concentrations. For example, the presence of drugs, narcotics, hormones, steroids, polypeptides, prostaglandins or infectious organisms in blood, urine, saliva, vaginal secretions, seminal fluids and other biological fluids has to be determined in an accurate and rapid fashion for suitable diagnosis or treatment.

To provide such determinations, various methods have been devised for isolating and identifying biological substances employing specific binding reactions between the substance to be detected (identified as a "ligand" herein) and compounds specifically reactive with that substance (identified as "receptors" herein). Radioactive or enzyme labels have been used to detect the resulting reactive complex.

One particular type of test which has been developed is what is known in the art as an immunometric or a "sandwich" assay. Such an assay involves "sandwiching" the ligand (such as an antigen) with two or more receptor molecules (such as antibodies) which complex with the compound in a non-interfering manner and at different epitopic sites. Examples of such assays are described in U.S. Pat. No. 4,486,530 (issued Dec. 4, 1984 to David et al) where monoclonal antibodies having high affinity are used. In most sandwich assays, one or more of the receptor molecules are suitably immobilized on an insoluble carrier such as small particles, membranes, plates, or similar objects, as described in U.S. Pat. No. 4,496,654 (issued Jan. 29, 1985 to Katz et al) where a biotinylated antibody is immobilized on an avidin coated support. U.K. Patent No. 2,074,727 describes sandwich assays in which the complex of antigen and antibodies formed is or will be insolubilized at the time of or subsequent to complex formation.

One ligand of particular interest is human chorionic gonadotropin (hCG), a hormone which increases in concentration in a human female soon after conception. It is desirable to measure hCG at the appropriate concentrations in order to detect pregnancy early. A very useful assay and test device for hCG determination is described in copending and commonly assigned U.S. Ser. No. 136,211, filed by Smith-Lewis on Dec. 18, 1987. That assay utilizes a biotinylated antibody to hCG which is immobilized in the test device using an acrylamide polymer. In that assay, as well as others known in the art, a wash solution is used to separate complexed materials from uncomplexed materials.

It has been observed, however, that the contents of the wash solution used can affect background in the test. Unwanted background (that is, detectable species from sources other than hCG) makes it difficult to detect low hCG concentrations. In other words, it reduces assay sensitivity. Moreover, if background is consistently high enough, there may be a high incidence of false results in assays.

It would be highly desirable to have a highly sensitive and rapid test for an immunological ligand, especially hCG, in test specimens which is not prone to high background.

SUMMARY OF THE INVENTION

The problems of high background in analytical procedures for immunological ligands, have been overcome by using an aqueous wash solution buffered to a pH of from about 5 to about 9 and comprising at least about 0.01 weight percent of a compound comprising a dodecyl sulfate anion and an alkali metal or ammonium cation.

This wash solution can be included in a test kit useful for the determination of an immunological ligand comprising:

(a) one or more receptors for an immunological ligand, at least one of which is labeled for detection, and (b) the aqueous wash solution described above.

This invention also provides a method for the determination of an immunological ligand comprising the steps of:

A. contacting a specimen suspected of containing an immunological ligand with one or more receptors for the ligand, at least one of which is labeled for detection, to form a detectable immunological complex between the ligand and the one or more receptors, B. separating the detectable complex from uncomplexed materials by washing the complex with the aqueous wash solution described above, and C. detecting either the amount of detectable complex or uncomplexed labeled receptor.

The wash solution of this invention provides a means for keeping background very low in assays, especially assays for immunological ligands, such as hCG. The critical feature of this wash solution is the presence of at least about 0.01 weight percent of a compound comprising a dodecyl sulfate anion and an alkali metal or ammonium cation. A particularly useful compound is sodium dodecyl sulfate. It is uncertain as to the mechanism for this advantage, but it is apparent from the example below that compounds structurally similar to the dodecyl compound do not provide the same result. It should also be noted that this wash solution is shown in Example 1 of U.S. Ser. No. 136,211 (noted above), but no appreciation of this advantage is evident in that application.

DETAILED DESCRIPTION OF THE INVENTION

The present invention provides a wash solution, test kit and method for use in analytical methods whereby a detectable immunological complex between ligand and receptor is formed. As noted above, an immunological ligand is a compound of biological interest which is to be detected. Specific examples of ligands are described below. A receptor is a compound which specifically complexes with the ligand. The method can be used to provide a rapid determination so that an assay can be performed in a doctor's office or in a consumer's home to provide immediate results. The assay can be used to detect the presence or absence of a mono- or multivalent or multideterminant ligand. Preferably, it is used to detect a multideterminant ligand, such as hCG. A monovalent ligand has a single epitopic site for complexation with a receptor. A multivalent ligand has two or more epitopic sites for complexing with a multiplicity of the same receptor. A multideterminant ligand has two or more epitopic sites for complexing with two or more different receptors.

More specifically, the present invention can be used in the determination of an immunological ligand in test specimens to which there are naturally occurring or synthetically produced specific binding receptors. This determination can be made by merely determining the presence or absence of the ligand, or by quantitatively determining the amount of ligand. In particular, the invention can be used to assay biological fluids of animals, humans or plants, but preferably of humans. Such fluids include, but are not limited to, whole blood, plasma, sera, lymph, bile, urine, spinal fluid, seminal fluid, lacrimal fluid, vaginal secretions, sputum, perspiration and the like as well as stool specimens. It is also possible to assay fluid preparations of human or animal tissue such as skeletal muscle, heart, kidney, lungs, brains, bone marrow, skin and the like.

An immunological ligand is broadly defined as an immunological species which is (1) any substance which, when presented to an immunocompetent host, will result in the production of a specific antibody capable of binding with that substance, or (2) the antibody so produced, which ligand participates in an antigen-antibody reaction.

Representative immunological ligands detectable using the wash solution of the present invention include primary amines, amino acids, peptides, polypeptides, proteins, lipoproteins, glycoproteins, drugs, haptens, enzymes, steroids, lipids, nucleic acids, hormones, vitamins, polysaccharides, glycolipids, alkaloids, organisms [bacteria (for example, Streptococcus A), protozoa, fungi, viruses (for example, retroviruses such as HTLV-I or HIV-I, or herpes viruses such as herpes simplex viruses I and II), rickettsia and the like] and components thereof, blood components, tissue and organ antigens and other materials known to one skilled in the art.

In some instances, the ligand is an antibody which is directed against a drug, hormone, antibiotic or other compound having antigenic properties. In such instances, the receptor is an antigenic material which specifically complexes with the antibody of interest. Where the ligand is an antigen and the receptor is an antibody, either monoclonal or polyclonal antibodies can be used, and they can be whole molecules or various fragments thereof. Preferably, biotinylated monoclonal antibodies are used in the present invention. In other instances, the ligand is an antibody and the receptor is an anti-antibody.

In a preferred embodiment, the invention is useful for the detection of hCG as an early indicator of pregnancy. In this embodiment, one or more different antibodies to hCG are reacted with the antigen to form an immunological complex. One of the antibodies is labeled suitably for detection. Uncomplexed materials are then removed from the detectable complex using the wash solution of the present invention, followed by appropriate detection procedures. Preferably, the antibodies are immobilized in a test device, as described below, in order to provide reagents for forming the complex with hCG at different epitopic sites in a convenient format. Most preferably, at least one of these antibodies is biotinylated and the other is labeled.

The wash solution of this invention is an aqueous buffered solution which advantageously keeps background low in assays. It is generally used to aid in the separation of uncomplexed materials from immunological complexes. Contained in the wash solution is an ionic compound comprising a dodecyl sulfate anion and a cation selected from the alkali metal and ammonium cations. Particularly useful alkali metal cations include lithium, sodium and potassium. Representative ionic compounds include ammonium dodecyl sulfate, sodium dodecyl sulfate, potassium dodecyl sulfate, rubidium dodecyl sulfate and lithium dodecyl sulfate. Sodium dodecyl sulfate is a most useful ionic compound.

The ionic compound identified above is present in the wash solution in a concentration of at least about 0.01, and preferably from about 0.15 to about 1, weight percent (based on total solution weight). The solution is buffered with one or more suitable buffers to a pH of from about 5 to about 9, and preferably to a pH of from about 7 to about 8. Useful buffers include sodium phosphate, N-(2-acetamido)-2-aminoethanesulfonic acid, N,N-bis(2-hydroxyethyl)glycine, 4-(2-hydroxyethyl)-1-piperazineethanesulfonic acid, 4-morpholineethanesulfonic acid, 4-morpholinepropanesulfonic acid, 2-[tris(hydroxymethyl)-methylamino]-1-ethanesulfonic acid, N-[tris(hydroxymethyl)methyl]glycine, tris(hydroxymethyl)aminomethane, and others known in the art. Sodium phosphate buffer is preferred. Use of the wash solution is described below.

As noted above, the kit of the present invention includes the wash solution described herein, as well as one or more receptors for the ligand, one of which is labeled for detection. Where the label is an enzyme, the kit can also contain a suitable detection system reactive with the enzyme to provide a detectable species (for example, a dye).

The assay of this invention is usually carried out using a test device in which the complexed material is detected. Such devices can be included as part of the kit, if desired, and can be as simple as a test strip, test slide, filter paper, test tube, petri dish, dip stick and the like, but more usually, it is a disposable test device having one or more test zones or wells for analytical use. Such a device comprises a water-insoluble substrate which is chemically and immunologically inert (that is, nonreactive) with the ligand, receptor or other reagents used in the assay. The substrate can be a flat or configured material which will accommodate one or more reagents and which can be contacted in some manner with a test specimen. Either the test specimen can be added to the device, such as a test tube or microtest plate, or the device can be added to the specimen or otherwise contacted for a period of time sufficient for the assay to occur. The device can be disposable or reusable.

In one embodiment, the device can be used to react ligand and receptor, but the resulting complex is then put into a second device in which the amount of ligand is determined in a suitable fashion. Alternatively, the device can be a device where all steps of the assay are carried out, such as a microtest plate having a multiplicity of preformed test wells. Various test devices are known in the art including U.S. Pat. No. 3,825,410 (issued July 23, 1974 to Bagshawe), U.S. Pat. No. 3,888,629 (issued June 10, 1975 to Bagshawe), U.S. Pat. No. 3,970,429 (issued July 20, 1976 to Updike) and U.S. Pat. No. 4,446,232 (issued May 1, 1984 to Liotta). Particularly useful devices are described in copending and commonly assigned U.S. Ser. No. 98,248, filed Sept. 18, 1987 by Hinckley et al and in commonly assigned U.S. Ser. No. 136,211, noted above, the disclosures of both of which are incorporated herein by reference.

More specifically, the test device comprises a water-insoluble substrate having one or more test zones therein each of which can accommodate a sample of a biological specimen and appropriate reagents.

The substrate can be prepared from any useful water-insoluble material such as glass, polymeric materials, fibrous materials, cellulosic materials and other materials known in the art.

In a preferred embodiment, the test device has three test zones or wells designed for providing a test result and positive and negative control results. Such a device would be particularly useful in a doctor's office or in a consumer's home as part of a diagnostic kit, such as a pregnancy test kit. Another test device is described and claimed in copending and commonly assigned U.S. Ser. No. 19,810, filed Feb. 27, 1987 by Hinckley. Other variations of useful test devices would be within the purview of a worker of ordinary skill in the art. Preferably, the test device has a water-insoluble microporous filtration membrane in each test well for filtering out immunological complex from uncomplexed materials and specimen fluid.

The device of this invention is adaptable to any assay using suitable chemical and biological reagents. In a preferred embodiment, one or more antibodies (for example, a biotinylated or labeled antibody, or both) for hCG are immobilized within the device as described and claimed in U.S. Ser. No. 136,211, noted above, for the detection of hCG in a urine specimen.

As noted above, the kit of this invention can also include a detection system for detecting the formation of an immunological complex. This system can be as simple as a second receptor for the ligand which is suitably labeled for detection. Useful detection labels include, but are not limited to, radioisotopes, chemiluminescent compounds, bioluminescent compounds, fluorescent compounds, colored beads, dyes, dye precursors and enzymes. Many useful labels are described in the art, for example, in E.P. Publication No. 201,079. These labels can be detected using suitable reagents, equipment and procedures.

Preferably, the label is an enzyme (for example, peroxidase, alkaline phosphatase, malate dehydrogenase, glucose oxidase, urease, catalase or glucose-6-phosphate dehydrogenase). In such a case, the detection system includes an enzyme substrate and a dye forming reagent if needed. Reaction of the enzyme with the substrate may provide a detectable species. Alternatively, the enzymatic reaction may only begin a series of reactions involving other reagents to provide a detectable species, such as a dye.

For example, when peroxidase is used as a label, the kit could also include hydrogen peroxide and appropriate dye forming reagents, such as a tetramethylbenzidine or a leuco dye which provides a dye in the presence of hydrogen peroxide and peroxidase [for example, a triarylimidazole leuco dye as described in U.S. Pat. No. 4,089,747 (issued May 16, 1978 to Bruschi) or a triarylmethane leuco dye as described in U.S. Pat. No. 4,670,385 (issued June 2, 1987 to Babb et al)]. A preferred dye-providing composition is described and claimed in my copending and commonly assigned U.S. Ser. No. 136,166, filed Dec. 18, 1987. Useful substrates and dye forming reagents for other useful enzymes are well within the skill of an ordinary worker in the art.

In a preferred embodiment of this invention, the test kit comprises:
(a) a test device described above having a multiplicity of test wells, and having immobilized in at least one of the test wells, an antibody reactive with hCG at a first epitopic site and which is in dry form,
(b) a second antibody reactive with hCG at a second epitopic site and which is labeled with peroxidase,
(c) a detection system reactive with peroxidase, and
(d) the wash solution of this invention.

The antibody in the test device can be rendered insoluble by immobilizing it on a water-insoluble substrate, such as a surface of the test device, a membrane, glass or polymeric particles, or other materials as is known in the art. More preferably, it is a water-soluble biotinylated antibody which is immobilized in an admixture with a binder material as described in U.S. Ser. No. 136,211, noted above. The antibody is capable of being insolubilized by means of an avidin-biotin reaction using an insolubilizing reagent comprising an insoluble phase to which avidin or a derivative thereof is bound. This insolubilizing reagent can be included in the test kit if desired.

Such an insolubilizing reagent has an insoluble phase, such as glass beads, metal particles, membranes, polymeric beads, glass or cellulosic fibers, and other known in the art, to which are attached molecules of avidin or a derivative thereof, such as streptavidin, succinylated avidin, monomeric avidin and the like. A preferred insolubilizing reagent useful in the practice of this invention is described in copending and commonly assigned U.S. Ser. No. 136,165, filed Dec. 18, 1987 by Sutton et al. A representative reagent is described and used in the example below. These preferred reagents are prepared by covalently attaching avidin to the insoluble phase, for example, polymeric beads, through activated 2-substituted ethylsulfonyl or vinylsulfonyl groups or active halogen atoms.

Avidin or a derivative thereof can be attached to an insoluble phase in any suitable fashion known in the art, for example, as described in U.S. Pat. Nos. 4,298,685 (noted above), 4,496,654 (noted above) and 4,582,810 (issued Apr. 15, 1986 to Rosenstein) and PCT Publication No. 84/03358 (published Aug. 30, 1984). The avidin can be attached by adsorption, but preferably it is attached covalently by reaction of reactive moieties in the avidin molecule (such as reactive amine groups) with the appropriate reactive groups on the carrier (such as carboxyl, halomethyl, vinylsulfonyl or chloroethylsulfonyl).

The kit of the present invention can also include optional reagents and equipment such as other wash solutions, buffer solutions, reagent solutions, bottles, pipettes, devices for prefiltering specimens and other materials known in the art which facilitate kit use.

Generally, the method of this invention is carried out by contacting a specimen suspected of containing the ligand with one or more receptors to the ligand to form an immunological complex, at least one of the receptors being labeled so the complex is detectable. The complex is then separated from uncomplexed materials by washing the complex with the wash solution of this invention. After separation, either the complex or the uncomplexed materials are detected using the appropriate detection equipment and procedures, for example using light scattering, colorimetric, fluorometric, radiometric or other techniques. It is best to perform this assay at a temperature above about 10° C.

It is desirable in this method that, prior to, simultaneously with or subsequent to the contact of specimen with the receptor, the specimen is put into a test device as described above, and the uncomplexed materials are wash through the filtration membrane while the immunological complex is retained on the membrane. It is desirable also that the complex be insolubilized at some time prior to the wash step. For example, one of the receptors can be attached to an insoluble substrate initially. Alternatively and preferably, the insolubilizing reagent described above is used to insolubilize the complex after its formation using an avidin-biotin reaction.

For the detection of hCG, the method is carried out by contacting a specimen (usually urine) suspected of containing hCG with one or more different antibodies to hCG in an appropriate test device. One of the antibodies is suitably labeled for detection. The complex is separated from the uncomplexed materials using the wash solution of this invention, and suitable detection procedures are performed. This method can be readily practiced in a doctor's office or at home for early determination of pregnancy by assaying urine samples.

The following example is representative of the practice of this invention but is not intended to limit the scope of this invention.

Materials

Antibody-biotin conjugates were prepared using anti-hCG monoclonal antibodies obtained from Immuno-Search, Inc. (Toms River, N.J.) and biotin N-hydroxysuccinimide obtained from Calbiochem-Behring Corp. using the method described by Hofmann et al, *J.A.C.S.* 100, 3585 (1978).

Human chorionic gonadotropin (hCG) was obtained from Calbiochem (La Jolla, Calif.).

Antibody-peroxidase conjugates were prepared using anti-hCG monoclonal antibodies obtained from Cambridge Medical Diagnostics (Bellerica, Mass.) and horseradish peroxidase from Miles Laboratories (Elkhart, Ind.) by the method described by Yoshitake et al, *Eur. J. Biochem.* 101, 395 (1979).

A leuco dye solution was prepared with 2-(4-hydroxy-3,5-dimethoxyphenyl)-4,5-bis(4-methoxyphenyl)imidazole as follows:

Solid leuco dye (to make a 0.1% solution) was dissolved in a solution of 20% poly(vinyl pyrrolidone) in sodium phosphate buffer (5 mmolar). This solution was then added to a solution containing hydrogen peroxide (10 mmolar), 4'-hydroxyacetanilide electron transfer agent (5 mmolar) and diethylenetriaminepentaacetic acid chelating agent (10 $\mu$ molar) in sodium phosphate buffer to produce a final concentration of 1% poly(vinyl pyrrolidone) and 0.005% leuco dye.

Succinylated casein was prepared by reacting casein with an equal weight of succinic anhydride for four hours at 25° C., then purifying the product by dialysis.

The buffers mentioned and used herein are available from a number of commercial sources including Sigma Chemical Co. (St. Louis, Mo.).

EXAMPLE

Asay of Urine for hCG

This example, illustrating a method for detecting hCG in urine samples, is similar to Example 1 of U.S. Ser. No. 136,211, noted above, with the exception that the comparison provided herein was not described in that application, and no keeping tests are considered herein.

Preparation of Insolubilizing Reagent

The following procedure for attachment of avidin to an insoluble phase is taken from Example 1 of copending U.S. Ser. No. 136,165 of Sutton et al, noted above.

The three solutions outlined below were continuously added to a 1365 ml vessel containing deoxygenated water at 80° C. at the indicated rates:

Solution 1

Styrene (739 g), m & p-(2-chloroethylsulfonylmethyl)styrene (82 g) and 1-dodecanethiol (8.2 g) at 2.5 g/min. for 380 minutes.

Solution 2

Ammonium persulfate (19.7 g) and distilled, deoxygenated water (1152 g) at 2.14 g/min. for 380 minutes.

Solution 3

Sodium pyrosulfite (9.9 g) and distilled water (1152 g) at 2.27 g/min. for 380 minutes.

After 380 minutes, the reaction was stopped, yielding about 1218 g of latex at 33.4% solids. The latex was dialyzed for 3 days to yield a latex having 27.3% solids and a pH of 5. This latex was diluted to 13.5% solids. NMR analysis confirmed a 96:4 molar ratio of styrene to the second monomer. The resulting latex particles had an average diameter of about 0.67 $\mu$m as measured by transmission electron microscopy.

A sample (0.75 ml) of the latex described above was diluted to 20 ml with borate buffer (50 mmolar, pH 8.5) and avidin (5 mg, Sigma Chemical Co.) was subsequently added. The resulting suspension was agitated in an end-over-end fashion at 37° C. for 18 hours, followed by centrifugation. The supernatant was discarded and the particles washed once with buffer by centrifugation and resuspended in 10 ml borate buffer. Biotin binding analysis (that is, titration with tritium labeled biotin) indicated that avidin had been covalently attached to the particles ($7 \times 10^{-6}$ molar binding sites per 0.3% bead suspension) to form a reagent of the present invention.

Assay

All assays described herein were performed at room temperature (generally between 20° and 25° C.). Test devices, as described in U.S. Ser. No. 98,248 (noted above), were used to determine hCG in a urine specimen in the following manner. Each test device comprised: a negative control well to show background and to act as a reference test, a positive control well to indicate that the reagents and procedures were used properly, and a test well for the assay. Each test well contained a filter membrane consisting of a microporous nylon filtration membrane (obtained from Pall Corp.).

Each negative control test well contained 4-morpholinepropanesulfonic acid buffer (2 mg) and poly(acrylamide) binder (60 $\mu$g). The test well for the assay contained a dried coating of biotinylated anti-hCG antibodies (3 $\mu$g) immobilized in poly(acrylamide) binder (60 $\mu$g), and dried buffer (2 mg) in a different location in the test well. The positive control well contained biotinylated anti-hCG antibodies (3 $\mu$g) immobilized in poly(acrylamide) binder (60 $\mu$g), and dried hCG (400 mI.U.) in a separate location from the buffer (2 mg) in the test well.

Samples had been prefiltered to remove impurities and were known to contain about 30–300,000 I.U./1 of hCG. The samples were added to all wells of the test device, followed by the addition of a peroxidase-labeled monoclonal anti-hCG antibody (40 μl of a $10^{-9}$ molar solution) to each well. After a two minute incubation period, a suspension of the insoluble immunoreactive reagent described above (40 μl of a 0.6% dispersion) was added and fluid was allowed to drain through the membrane in each well.

The wash solution (200 μl) of this invention was prepared from sodium phosphate (0.1 molar, pH 7.2), Thiomersal antibiotic (0.01 weight percent) and sodium dodecyl sulfate (10 mmolar, 0.29 weight percent) and added to each well to wash away uncomplexed materials. The leuco dye solution described above (40 μl) was then added to each well. After two minutes, the color formed on each membrane was evaluated by reflectance measurements using standard equipment and the results were converted to transmittance density ($D_T$) using the Williams-Clapper transform. The color was also evaluated by comparing it to color values on a color gradient chart (values of 0 to 10, with 10 representing the densest color). A dark red color was seen in the test and positive control wells indicating the presence of hCG in the urine speciment. The negative control well of the device was graded as shown in Table II using the color gradient chart.

The same test was performed using the same test device and procedure but substituting various known anionic surfactants for sodium dodecyl sulfate in the wash solution. Table I below lists the materials substituted in the Control A-F wash solutions. Control G contained no surfactant. From Table II, which shows the background data observed with each assay, it is apparent that the assays using the Control wash solutions exhibited unacceptably high background. Yet, use of the wash solution of this invention unexpectedly reduced the background to acceptable levels.

TABLE I

| Assay | Wash Solution Surfactant |
| --- | --- |
| Invention | Sodium dodecyl sulfate (available from Eastman Kodak Co.) |
| Control A | Polyether sulfonate of aliphatic alcohols (available as AVANEL S-70 from PPG Industries) |
| Control B | Dihexyl sodium sulfosuccinate (available as MONAWET MM-80 from Mona Industries, Inc.) |
| Control C | Sodium laurylether sulfate (available as POLYSTEP B-12 from Stepan Co.) |
| Control D | Sulfated polyether of lauryl alcohol (available as STANDAPEL 125-E from Henkel Corp.) |
| Control E | $C_{14}$-$C_{17}$ alkyl sulfonate mixture (available as HOSTAPUR SAS-90 from American Hoechst Corp.) |
| Control F | Sodium decyl sulfate (available from Eastman Kodak Co.) |
| Control G | Phosphate buffer only. |

TABLE II

| Assay | hCG Concentration (I.U./l) | *Background (negative Control) |
| --- | --- | --- |
| Invention | 30 | 0 |
|  | 50 | ½ |
|  | 20,000 | 0 |
|  | 300,000 | 0 |
| Control A | 50 | 2 |
|  | 300,000 | 4 |
| Control B | 50 | ½ |
|  | 300,000 | 1 |
| Control C | 50 | 2 |
|  | 300,000 | 2 |
| Control D | 50 | 4 |
|  | 300,000 | 3 |
| Control E | 50 | ½ |
|  | 300,000 | ½ |
| Control F | 50 | 1 |
|  | 300,000 | 1 |
| Control G | 30 | 4 |
|  | 50 | 4 |
|  | 300,000 | 4 |

*Background as measured using the color gradient chart. In the negative control well, it must be as close to 0 as possible over the hCG concentration range. A background of ½ is marginal, and acceptable only if it is a random result.

The invention has been described in detail with particular reference to preferred embodiments thereof, but it will be understood that variations and modifications can be effected within the spirit and scope of the invention.

I claim:

1. A method for the determination of an immunological ligand comprising the steps of:
   A. contacting a specimen suspected of containing an immunological ligand with one or more receptors to said ligand, at least one of which is labeled for detection, to form a detectable immunological complex between said ligand and said one or more receptors,
   B. separating said detectable complex from uncomplexed materials by washing with an aqueous wash solution buffered to a pH of from about 5 to about 9 and comprising at least about 0.01 weight percent of a compound comprising a dodecyl sulfate anion and an alkali metal or ammonium cation, and
   C. detecting either the amount of detectable complex or uncomplexed labeled receptor as a determination of said immunological ligand.

2. The method of claim 1 for the determination of hCG wherein said one or more receptors are antibodies to hCG.

3. A method for the determination of hCG comprising the steps of:
   A. contacting a specimen suspected of containing hCG with one or more different antibodies to hCG, at least one of which is labeled for detection, to form a detectable immunological complex between hCG and said one or more antibodies,
   B. prior to, simultaneously with or subsequent to said contacting step A, applying said specimen to a test device containing a water-insoluble microporous filtration membrane,
   C. washing uncomplexed materials through said filtration membrane while retaining said detectable complex on said membrane, the washing is accomplished with an aqueous wash solution buffered to a pH of from about 5 to about 9 and comprising at least about 0.01 weight percent of a compound comprising a dodecyl sulfate anion and an alkali metal or ammonium cation, and D. detecting either the amount of detectable complex or uncomplexed labeled antibody as a determination of hCG in said specimen.

4. The method of claim 3 wherein, prior to said washing step C, hCG in said specimen is insolubilized with an unlabeled antibody to hCG which is or is capable of becoming attached to an insoluble phase.

5. The method of claim 3 wherein said label is an enzyme, and said detectable complex is detected by contacting it with a substrate for said enzyme and a dye forming reagent which provides a dye upon enzymatic reaction of enzyme on said substrate.

6. The method of claim 3 wherein said washing is accomplished with a wash solution buffered to a pH of from about 7 to about 8 and said dodecyl sulfate compound is sodium dodecyl sulfate which is present in an amount of from about 0.15 to about 1 weight percent.

7. A method for the determination of hCG comprising the steps of:
    A. contacting a specimen suspected of containing hCG with a test device comprising a water-insoluble substrate having one or more test wells each of which contains a water-insoluble microporous filtration membrane, and having immobilized in at least one of said test wells, a biotinylated antibody reactive with hCG at a first epitopic site and which is in dry form, to form a reaction product of hCG with said biotinylated antibody,
    B. prior to, simultaneously with or subsequent to said contacting step (A), contacting said specimen with a second antibody reactive with hCG at a second epitopic site and which is enzyme labeled, to form a detectable complex of hCG with said first and second antibodies,
    C. contacting said complex with an insolubilizing reagent comprising an insoluble phase to which avidin is bound, to form an insolubilized complex through reaction of avidin with biotin,
    D. separating the resulting labeled, insolubilized complex from uncomplexed materials, by washing unreacted materials through said filtration membrane with a wash solution buffered to a pH of from about 7 to about 8 and containing from about 0.15 to about 1 weight percent of sodium dodecyl sulfate, and
    E. determining the amount of detectable complex on said filtration membrane by contacting said insoluble complex with a substrate for said enzyme and a dye forming reagent which provides a dye upon enzymatic reaction of said enzyme on said substrate as a determination of hCG in said specimen.

8. The method of claim 7 wherein said specimen is urine.

9. A test kit useful for the determination of hCG comprising:
    (a) a test device comprising a water-insoluble polymeric substrate having a multiplicity of test wells, and having immobilized in at least one of said test wells, a biotinylated antibody reactive with hCG at a first epitopic site and which is in dry form,
    (b) a second antibody reactive with hCG at a second epitopic site and which is labeled with peroxidase,
    (c) a detection system reactive with peroxidase,
    (d) an insolubilizing reagent comprising an insoluble phase to which avidin or a derivative thereof is bound, and
    (e) an aqueous wash solution buffered to a pH of from about 5 to about 9 and comprising at least about 0.01 weight percent of a compound comprising a dodecyl sulfate anion and an alkali metal or ammonium cation.

10. The test kit of claim 9 wherein said wash solution is buffered to a pH of from about 7 to about 8 and said dodecyl sulfate compound is sodium dodecyl sulfate which is present in an amount of from about 0.15 to about 1 weight percent.

11. The test kit of claim 10 wherein said wash solution is buffered with sodium phosphate buffer.

* * * * *